(12) United States Patent
Tanghøj

(10) Patent No.: US 9,511,204 B2
(45) Date of Patent: Dec. 6, 2016

(54) CATHETER ASSEMBLY

(71) Applicant: Coloplast A/S, Humlebaek (DK)

(72) Inventor: Allan Tanghøj, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/835,837

(22) Filed: Aug. 26, 2015

(65) Prior Publication Data

US 2015/0359994 A1     Dec. 17, 2015

Related U.S. Application Data

(63) Continuation of application No. 14/001,511, filed as application No. PCT/DK2012/050080 on Mar. 16, 2012, now Pat. No. 9,144,659.

(30) Foreign Application Priority Data

Mar. 18, 2011   (DK) ................... 2011 70128

(51) Int. Cl.
| | |
|---|---|
| *B65D 83/10* | (2006.01) |
| *A61M 25/00* | (2006.01) |
| *B65D 65/14* | (2006.01) |
| *B65D 65/22* | (2006.01) |

(52) U.S. Cl.
CPC ....... *A61M 25/002* (2013.01); *A61M 25/0017* (2013.01); *B65D 65/14* (2013.01); *B65D 65/22* (2013.01)

(58) Field of Classification Search
CPC ...... B65D 65/14; B65D 65/22; A61M 25/002; A61M 25/0017
USPC 206/363–369, 438, 571, 817; 220/480–482; 221/56, 226, 229, 247, 279; 604/163, 171, 172, 265, 272, 544
See application file for complete search history.

(56) References Cited

U.S. PATENT DOCUMENTS

| | | | | |
|---|---|---|---|---|
| 1,007,804 | A | * 11/1911 | Schimmel | ................. A61L 2/26 206/210 |
| 1,518,531 | A | * 12/1924 | Lung | .................... A61M 5/3202 206/365 |
| 2,522,061 | A | 9/1950 | Rioux | |
| 2,620,061 | A | 12/1952 | Uxa | |
| 2,710,688 | A | * 6/1955 | Drey | .................... B65D 33/004 206/210 |
| 2,947,415 | A | * 8/1960 | Garth | ...................... A61L 2/206 206/364 |

(Continued)

FOREIGN PATENT DOCUMENTS

| | | |
|---|---|---|
| CN | 1997419 | 7/2007 |
| DE | 2015044 A1 | 9/1971 |

(Continued)

*Primary Examiner* — Luan K Bui
(74) *Attorney, Agent, or Firm* — Coloplast Corp., Coloplast A/S; Nick Baumann

(57) ABSTRACT

A catheter assembly includes a catheter attached to a connector and a package. The catheter has a proximal end sized for insertion into a bladder though a urethra and a distal end opposite of the proximal end. The connector is attached to the distal end of the catheter. The package is sized to receive the catheter and the connector, with the package including an opening sized for removal of the catheter and the connector from the package. A tab is placed over the opening of the package to seal the catheter and the connector inside of the package. An extractor has a first portion connected to the tab and a second portion coupled to the catheter proximal of the connector.

9 Claims, 2 Drawing Sheets

(56) References Cited

U.S. PATENT DOCUMENTS

| | | | |
|---|---|---|---|
| 3,035,691 A | | 5/1962 | Rasmussen et al. |
| 3,203,545 A | * | 8/1965 | Grossman ............ A61M 25/002 |
| | | | 206/210 |
| 3,410,455 A | | 11/1968 | Haas |
| 3,761,013 A | * | 9/1973 | Schuster ............. A61M 25/002 |
| | | | 206/439 |
| 3,889,808 A | | 6/1975 | Helms |
| 4,216,860 A | | 8/1980 | Heimann |
| 4,811,847 A | | 3/1989 | Reif et al. |
| 5,048,720 A | | 9/1991 | Hoke |
| 5,071,033 A | | 12/1991 | Siwek |
| 6,267,231 B1 | * | 7/2001 | Burns ................... B65D 83/02 |
| | | | 206/363 |
| 6,355,004 B1 | | 3/2002 | Pedersen et al. |
| 6,695,831 B1 | | 2/2004 | Tsukada et al. |
| 7,380,658 B2 | | 6/2008 | Murray et al. |
| 2004/0155053 A1 | | 8/2004 | Sanchez |
| 2005/0070882 A1 | | 3/2005 | McBride |
| 2005/0109648 A1 | * | 5/2005 | Kerzman ........... A61M 25/0111 |
| | | | 206/364 |
| 2011/0056852 A1 | * | 3/2011 | Frojd .................. A61M 25/002 |
| | | | 206/210 |
| 2011/0060317 A1 | | 3/2011 | Froejd |
| 2011/0114520 A1 | * | 5/2011 | Matthison-Hansen A61M 25/002 |
| | | | 206/364 |

FOREIGN PATENT DOCUMENTS

| | | |
|---|---|---|
| EP | 2106821 A1 | 10/2009 |
| RU | 184573 | 12/1997 |
| WO | 9747349 | 12/1997 |
| WO | 9811932 | 3/1998 |
| WO | 03002179 A2 | 1/2003 |
| WO | 03092779 | 11/2003 |
| WO | 2004054653 A1 | 7/2004 |
| WO | 2005092419 A1 | 10/2005 |
| WO | 2006009509 | 1/2006 |
| WO | 2006119781 A1 | 11/2006 |
| WO | 2010006619 A1 | 1/2010 |
| WO | 2010006620 A1 | 1/2010 |
| WO | 2011026930 | 3/2011 |

* cited by examiner

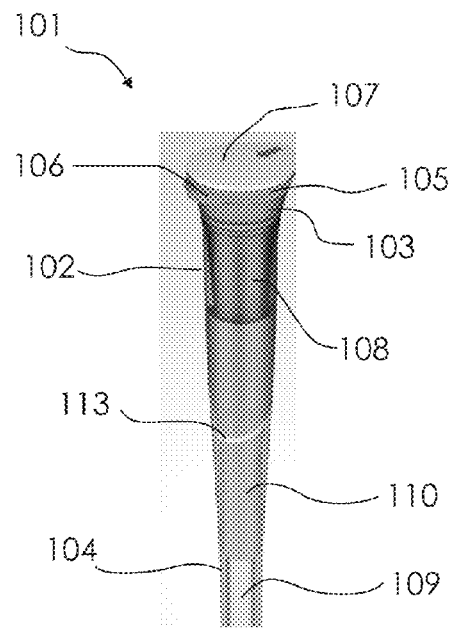
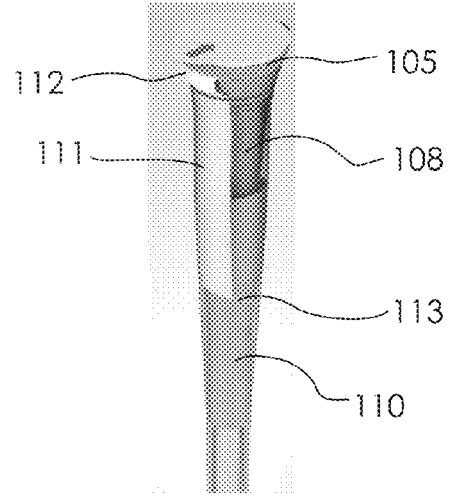
Fig. 3a    Fig. 3b
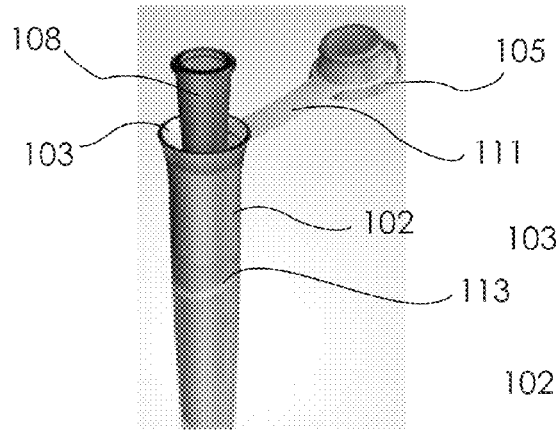
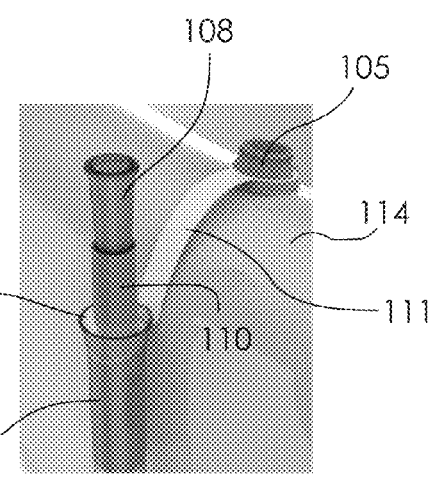
Fig. 4    Fig. 5

CATHETER ASSEMBLY

This is a CON of application Ser. No. 14/001,511, Filed Aug. 26, 2013, U.S. Pat. No. 9,144,659.

The invention relates to a catheter assembly comprising a catheter having a proximal end adapted to be inserted into a bodily cavity and a distal end having a drainage outlet, a catheter package having a cavity for accommodating the catheter and an opening for withdrawing the catheter from the package.

BACKGROUND

Catheters or especially intermittent urinary catheters are medical devices that are used to drain urine from the urinary bladder in situations where the users are not capable of voiding their bladders or where users have afflictions that cause problems in emptying their bladders.

Intermittent urinary catheters are often single use catheters that are provided with a lubricant, such as a gel lubricant, or the catheters may be provided with a surface coating that provides a low-friction surface on the catheter, such as a catheter having a hydrophilic coating. A frequent side effect of using catheters, including single use catheters is that users have a higher risk of getting a urinary tract infection, which may often be caused by bacteria that come into contact with the catheter prior to insertion. In an attempt to reduce the risk of contracting a urinary tract infection, single use catheters are often provided in sterile packages that maintain the catheters sterile until the user intends to use the catheter and opens the package.

When a sterile catheter package has been opened, there are a number of different scenarios the user may have to face. If the catheter is a gel lubricated catheter, the user has to withdraw the catheter and apply the gel to the surface of the catheter prior to insertion. In a different situation, where the catheter is a dry hydrophilic catheter, the user has to pour water into the package for activating the coating and then withdraw the catheter from the package. In another situation, where the catheter is a ready to use catheter, the user withdraws the catheter from the package and prepares for insertion.

The conventional catheter packages are usually provided in the form of one or two sheets of film that has to be opened to access the catheter. This means that the user is forced to handle the catheter before use in order to withdraw the catheter from the package.

A large group of users of intermittent catheters are persons that have reduced motor skills, as they may have lost voluntary bladder control due to illnesses, such as spina bifida, or accidents that have caused damage to the spinal cord, resulting in either para - or tetraplegia. This group of users may have a reduced dexterity in their hands or fingers and may often struggle with the preparation and/or withdrawal of catheters from their packages, which may further lead to the contamination of the catheter due to the lack of control of their hand or finger movements.

DESCRIPTION OF RELATED ART

Patent document DE 2005 20009947 U discloses a catheter assembly comprising a package and a catheter, where the proximal end (insertable end) is pulled out of the package using a string that is attached to the distal end of the catheter, where the package is used as a urine container and the user does not have to touch the insertable part of the catheter before inserting the catheter. However, the use of such a package requires that the package is attached to the distal end of the catheter, as the user is not to touch the catheter.

SUMMARY OF THE INVENTION

The invention concerns a catheter package having extracting means coupled to the catheter, so that it gets easier for the user to remove the catheter from the package. Many catheter users have poor or at least reduced hand dexterity and may lack the ability to pinch with the fingers. They will therefore find it difficult to grab and seize hold of a distal end of a catheter (e.g. a connector), when the catheter is to be removed from the package. Thus, the invention provides a catheter assembly, which, among other objects, alleviates the above problem.

DETAILED DESCRIPTION OF THE INVENTION

In a first aspect, the invention relates to a catheter assembly comprising a catheter having a proximal end adapted to be inserted into a bodily cavity and a distal end having a drainage outlet, a catheter package having a cavity for accommodating the catheter and an opening for withdrawing the catheter from the package, and extracting means that are coupled to the catheter for extracting the distal end of the catheter out of the package.

The extracting means may be used to assist the user in extracting the catheter from the package, as some users have reduced hand or finger dexterity and it might be difficult for the users to operate the package, so that the distal end is accessible. This may be especially advantageous when the catheter package is of the kind where the package is formed in such a manner that the opening of the package only partly exposes the distal end of the urinary catheter. When the distal end is only partly exposed the user may be required to fold, bend, cut or stretch the package, so that the distal end becomes exposed, or the user may have to insert fingers into a small opening to access the distal end. The extracting means according to the present invention are advantageously readily accessible to the user, so the user may pull the distal end of the catheter out of the package prior to the complete extraction of the catheter from the package. By pulling the distal end out of the package, the distal end becomes fully accessible to the user, and even users having reduced dexterity will be able to grab the distal end, so that the catheter may be fully extracted from the package.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted. The same definitions apply to the package and container—the proximal end is the end storing the proximal end of the catheter and the distal end is the opposite end.

The longitudinal direction is the distal to the proximal end. The transverse direction is the direction perpendicular to the longitudinal direction, which corresponds to the direction across the shaft of the catheter.

The catheter described in this application may be used as a urinary catheter.

The catheter comprises a main tubular part extending from the distal end to the proximal end. The tip is positioned in the proximal end of the catheter and is provided as a rounded closed end of the tube constituting the main part of the catheter. The catheter may comprise a connector in the distal end and may in an embodiment comprise a flared end of the catheter, so that the diameter of the connector increases with respect to the tubular part. The catheter may also comprise a handle in the distal end, which has a length allowing the user to manipulate the catheter.

Usually catheters are from size 8 FR to size 18 FR.

Catheters of this invention may prior to use be provided with a hydrophilic coating so as to impart a low-friction insertion.

The hydrophilic coating may be provided only on the insertable part of the catheter. The hydrophilic surface coating is of the kind which, when hydrated or swelled using a swelling medium, reduces the friction on the surface area of the catheter which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight water) to being adhesive when the hydration level of the coating is reduced (<75% weight water).

The catheter package may comprise a medium for activating the hydrophilic surface coating of the catheter. The activating medium may be a water based substance, such as sterile water, saline-solution, or any water based liquid. Furthermore, the activating medium may be in the form of a vapour contributing material, such as a wetted sponge, woven or non-woven material comprising a vapour contributing liquid. By introducing a vapour contributing material into the package, the vapour will over time hydrate the hydrophilic coating ensuring that the coating is activated and that the hydrophilic coating provides a low-friction surface for the catheter.

In one embodiment of the invention, the drainage outlet may have a cross sectional diameter that is larger than the part of the catheter proximal to the drainage outlet. In this way the coupling between the catheter and the extracting means may be in the form of a frictional coupling or similar that utilizes the increased diameter of the catheter. Thus, the coupling part will stop in the vicinity of the drainage outlet and will not pass the drainage outlet and by pulling onto the extracting means the coupling will transfer the pulling force to the catheter and the catheter will be lifted using the extracting means.

In one embodiment of the invention, the extracting means may be arranged in a distal end of the catheter package. By arranging the extracting means in the distal end of the package, the catheter may be extracted out of the package along the longitudinal axis of the package. This means that the package may be opened in the distal end using a predefined opening in the package material or peel opening of a film layer package. Thus, when the extracting means are in the distal end of the package, the opening may be formed in such a way that the opening only disposes a part of the distal end of the catheter or no part of the distal end of the catheter and the distal end of the catheter is exposed when the extracting means are used to pull the catheter from the package. This simplifies the design and production of the catheter package, as the package does not need to have an opening having complex features that expose the distal end of the catheter when opened.

In one embodiment of the invention, the extracting means may be coupled to a part of the catheter that is distal to the proximal end and proximal to the distal end. This means that the extracting means are coupled to the catheter at different areas than the extreme end of the catheter, which means that the important parts of the catheter, such as the insertable tip or the drainage outlet are not blocked by the coupling part of the extracting means.

In one embodiment of the invention, the extracting means may be coupled to a distal part of the catheter that is approximately between 50-99 percent of the length of the catheter. Thus, the extracting means may be arranged to assist in pulling onto the distal end of the catheter. When the extracting means are pulled in a longitudinal direction away from the distal end, the transfer of the force from the extracting means to the catheter will have a balancing point that is in the distal half of the catheter and the risk of tipping the catheter while pulling onto it is minimized.

In one embodiment of the invention, the extracting means may be in the form of a strip that has at least a length that extends from a proximal end coupled to a coupling area of the catheter and a distal end abutting the opening of the catheter package. This means that when the catheter package is opened, the extracting means are readily accessible for the user at the package opening. Thus, after opening the package, the user may grab onto the extracting means and pull onto the extracting means to expose the distal end of the catheter, so that the distal end of the catheter may be gripped by the user for insertion. In other embodiments of the present invention, the distal end may be arranged to extend beyond the package opening, so when the package is opened the extracting means will extend beyond the opening.

In one embodiment of the invention, the extracting means may be in the form of a strip having a proximal end that surrounds the catheter and a distal free end. The strip may surround the catheter in such a way that when the extracting means are manoeuvred in a direction away from the distal end of the catheter, the force of the movement will be transferred to the catheter. Furthermore, when the user grabs the distal end of the catheter and pulls the catheter in a direction away from the extracting means, the extracting means will release its coupling to the catheter and the catheter will move in a free manner relative to the extracting means. This means that when the user manoeuvres the catheter from the package, the extracting means will release the catheter and the extracting means may remain inside the package while the catheter is being pulled out of the package.

In one embodiment of the invention, the proximal end of the strip that surrounds the catheter may have a diameter that is smaller than at least the distal end of the catheter. This means that when the extracting means are pulled, the extracting means will not slide off the catheter, as the reduced diameter will prevent the catheter from sliding off the extracting means.

In one embodiment of the invention, the opening of the catheter package may be provided with openable closing means that seals off the cavity of the catheter package from the ambient space. This means that during storage and prior to use the closing means will close off the catheter package, so that the catheter cannot be accessed by the user or by any outside contaminants. These closing means may be in the form of a plug, peel off opening means, or similar.

In one embodiment of the invention, the extracting means may be coupled to the openable closing means. By coupling the extracting means to the openable closing means it is possible to expose the distal end of the catheter in one simple movement, i.e. the opening of the package. Thus, when the closing means are pulled from the package, the pulling movement will transfer to the extracting means and via the extracting means to the catheter. This may be advantageous for users that have low dexterity in their fingers or hands, as the one movement of the closing means has a double function, i.e. opening the package and exposing the catheter for removal from the package.

In one embodiment of the present invention, the end of the extracting means may be coupled to the package. By coupling the extracting means to the package the extracting means may be fastened to the package in such a way that the extracting means may lift the distal end of the catheter from the opening of the package and that the extracting means will not be releasable from the package and the extracting means will therefore not be removable from the package, without the use of excessive force.

In one embodiment of the present invention, the end of the extracting means may be displaceably coupled to the package, so that the extracting means may be manoeuvred in a longitudinal direction along the longitudinal axis of the package, while the extracting means are coupled to the package. This means that the extracting means will slide along the package until the distal end of the catheter has been exposed and upon exposure the extracting means will remain in its position while the catheter is being extracted.

In one embodiment of the present invention, the closing means may be provided with fastening means for fastening the closing means to a surface area. This means that the closing means may be attached to a surface and the opening means may be directly coupled to the package or coupled to the extracting means, so that the attached closing means may support the entire weight of the catheter assembly. This allows the user to position the catheter assembly at a location where he can have an easier access for extracting the catheter from the package, as the user does not have to hold the catheter assembly in his hands or put it away before catheterization, as the assembly is already arranged at a location away from the user.

BRIEF DESCRIPTION OF THE DRAWING

In the following drawings the invention is explained in further detail where,

FIGS. 3a and 3b are perspective views of a distal end of a catheter package seen from the front and the back, respectively, FIG. 4 is a perspective view of a distal end of a catheter package seen from the front, where the package has been opened, and FIG. 5 is a perspective view of the same, attached to a surface area of a sink.

DETAILED DESCRIPTION OF THE DRAWING

Figure 1:
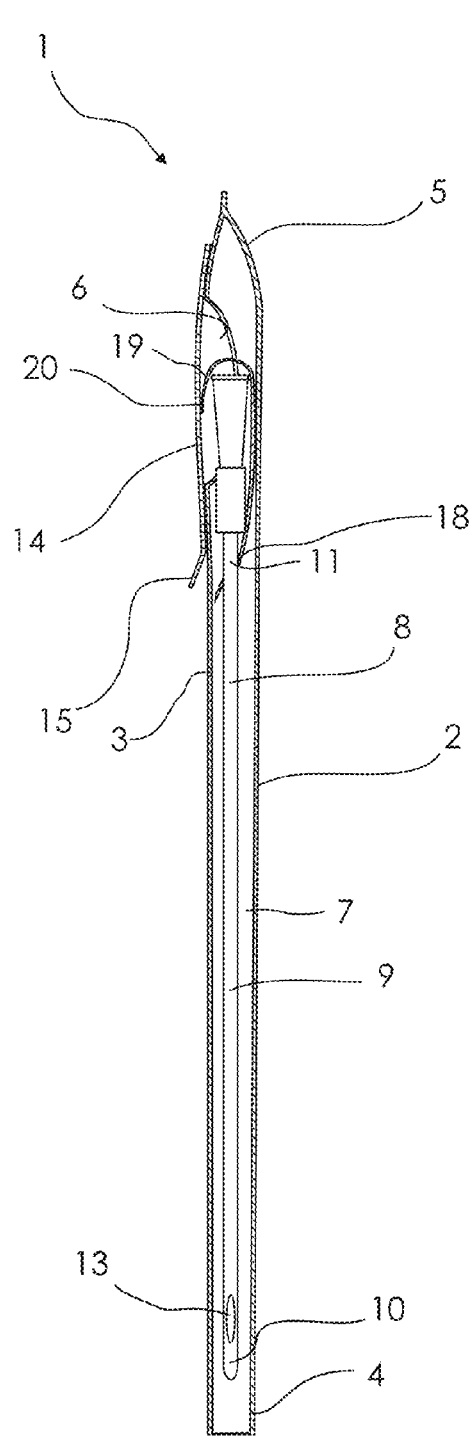
FIG. 1 is a side sectional view of a catheter assembly according to the present invention in a closed state.

FIG. 1 shows a sectional side view of a catheter assembly 1, where the catheter assembly is in the form of a catheter package 2 having a side wall 3, a proximal end 4 and a distal end 5, where an opening 6 in the side wall 3 is arranged close to the distal end of the catheter package. The catheter package 2 has an internal cavity 7 for holding a catheter 8. The catheter package is advantageously provided in a material that is flexible, so that the side walls of the package may be bent and flexed.

The catheter 8 is a conventional intermittent urinary catheter, having a catheter tube 9 for draining urine from the urine bladder of a user where a proximal end 10 of the catheter 8 is adapted to be inserted into a body cavity of a user. The opposite end of the catheter 8 the distal end 11 is provided with a connector 12 which acts as an outlet for urine drained through the catheter tube 9 and is in fluid communication via an inner lumen of the catheter tube 9 to at least one eyelet 13 arranged close to the proximal end of the catheter 8.

The opening 6 provides an entry into the internal cavity 7 of the catheter package 2 and when the catheter assembly is in its closed configuration, as shown in this figure, the opening 7 is sealed off using a closing means in the form of a peel-off tab 14. The peel-off tab 14 sealingly closes off the opening 6 by being bonded to the side wall 3 of the catheter package at the periphery of the opening 6. The tab 14 is provided with a gripping portion 15 that may be arranged in such a way that the user may easily grab onto the gripping portion, using his fingers, or it may be provided with a finger hole into which the user may insert his finger to get a firm hold of the gripping portion 15. The tab 14 is releasably bonded on the major part of its periphery to the side wall 3 of the package 2, while in an area 16 that is close to the distal end 5 of the package 2, the tab 14 is bonded more firmly, so that the tab 14 stays on the package 2 in the area 16 after the tab has been peeled 14 off the opening of the package 2 to provide access to the inner cavity 7 of the package 2.

Figure 2:
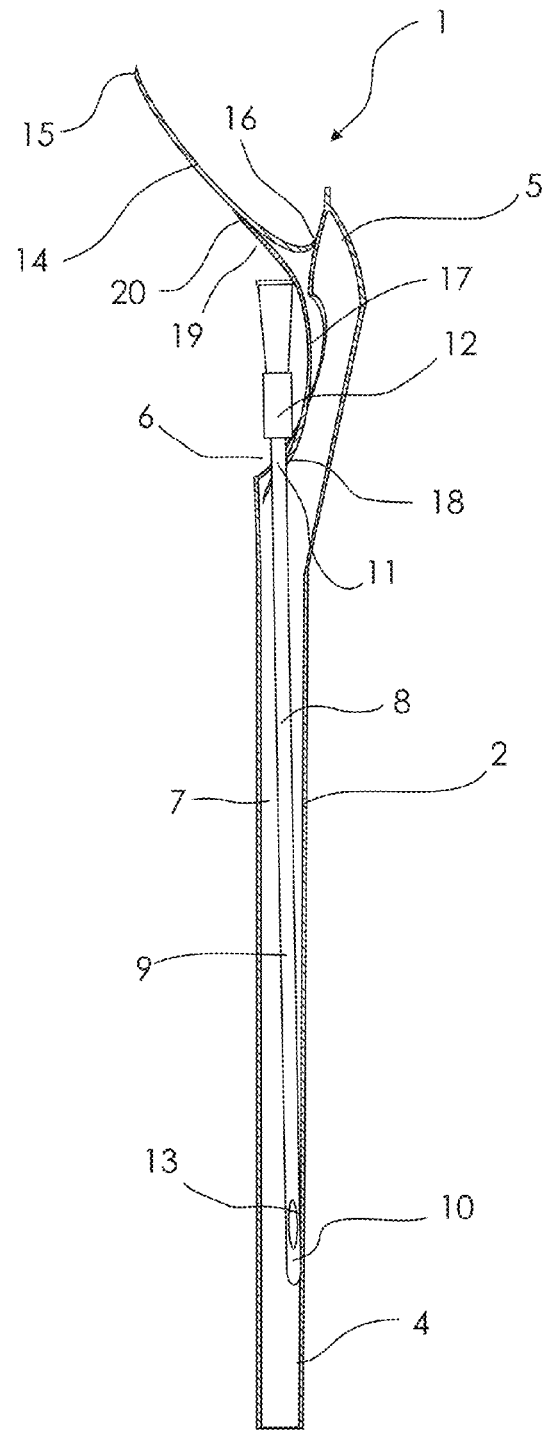
FIG. 2 is a side sectional view of a catheter assembly according to the present invention in an opened state.

The catheter assembly is further provided with an extraction member 17 that at one end 18 arranged around the distal end 11 of the catheter tube 8 and at the other end 19 attached to an inner wall of the peel-off tab 14 at attachment zone 20. The extraction member 17 mechanically couples the peel off tab 14 to the distal end 11 of the catheter tube 8, so that when the peel-off tab 14 is pulled off the package 14 the extraction member pulls onto the distal end 11 of the catheter tube 8 and pulls the connector 12 out of the package, so that the user has easy access to the catheter connector 12 in order to withdraw the catheter from the package before use. The opened position of the catheter assembly is shown in FIG. 2. The extraction member thus displaces the catheter in a longitudinal direction, lifting it up from the internal cavity of the package, so that the distal end of the catheter is easily accessible by the user.

The extraction member 17 is advantageously arranged behind the connector, as shown in FIGS. 1 and 2, in that the extraction member passes the connector inside the cavity close to the side wall of the package that is opposite the opening of the package. This means that when the peel-off tab 14 is opened in a manner as shown in FIG. 2 that is pulled in a distance away from the package, tension is applied to the extraction member and the centre of the extraction member pushes the connector out of the opening in the side wall in a direction that is orthogonal to the longitudinal axis of the catheter package. In related embodiments it is not the exact centre of the extraction member that pushes the connector out of the opening but rather a position near the centre of the extraction member.

FIG. 3a depicts another embodiment of the present invention, in perspective view seen from the front, showing a distal end 102 of a catheter assembly 101. The distal end 102 of the catheter assembly 101 is provided with an opening 103 providing access to the inner cavity 104 of the catheter assembly 101. In this embodiment, the opening 103 is provided in the extreme distal end of the catheter package, giving unhindered access in a longitudinal direction to the inner cavity 104 of the catheter package. The opening 103 is closed off using a cap 105, which sealingly closes off the opening 104 in at least a liquid tight manner, and possibly in a gas impermeable seal as well. The cap 105 is provided with a gripping member 106 in the form of a protrusion that facilitates the gripping of the cap 105 in order to push the cap 105 from the opening. Furthermore, the cap 105 may be provided with an adhesive area 107 that is arranged on the outer surface of the cap 105 in order to attach the outer surface of the cap 105 securely to a surface area of a sink, table, or similar structures available to the user when using the catheter assembly 101.

The distal end 102 of the catheter assembly is arranged in a funnel shape, so that the distal end has an inner diameter that is wide enough to hold a connector end 108 of a catheter 109 and to facilitate that the entire catheter may be arranged inside the catheter package. In this embodiment, the catheter 109 is further provided with an insertion aid 110 that is slidingly arranged around the catheter 109 and the catheter connector 108, so that the insertion aid may be manoeuvred in along the longitudinal axis of the catheter 109 during insertion of the catheter 109 into the body. The insertion aid 110 is in form of a generally tubular element arranged coaxially exterior of and around the catheter 109.

As shown in FIG. 3b, which is a perspective view from the back, the catheter assembly is further provided with an extracting means 111 which is in the form of a flexible strip 111 that is in one end 112 securely attached to the cap 105 and in the opposite end 113 is coupled to the insertion aid 110, so that the opposite 113 end is looped around the insertion aid 110. This means that the cap 105 is mechanically coupled to the distal end of the catheter 109 or the catheter connector 108, so when the cap is removed and manoeuvred in a direction away from the package, the extraction means will transfer the force from the cap to the catheter, causing the catheter to lift from the opening, giving the user access to the distal end of the catheter for the removal of the catheter from the catheter assembly, as shown in FIG. 4.

The opposite end 113 of the extracting means or the flexible strip may in a different embodiment be arranged around the catheter 109 or the connector 108 of the catheter, in embodiments where the insertion aid is not required or in embodiments where the insertion aid is arranged in a different manner.

As shown in FIG. 5, when the catheter assembly 101 has been opened, the adhesive area of the cap 105 may be used to secure the cap 105 to the surface area of a sink 114, so that the cap holds the catheter 109 and the catheter assembly 101 in easy reach for the user to extract the catheter 109 from the opening 103 by gripping the distal end or the connector 108 of the catheter. Thus, the user may prepare the catheter assembly for use by removing the cap from the catheter assembly, and the removal of the cap will cause the extracting member to pull onto the catheter, so that the catheter lifts from the catheter assembly, making the catheter easy to reach and easily gripped by the user.

Within the meaning of the present invention, any features that are shown in one embodiment may be applied to a different embodiment of the invention, such as the form and shape of the extracting member. Furthermore, the embodiments shown in the present invention may be adapted, so that the extraction member is not attached to the opening means of the package, but may be arranged separately inside the package, so that the user may open the package, and afterwards reach into the package to grab onto the extraction member to lift the distal end of the catheter from the package.

The invention claimed is:

1. A catheter assembly comprising:
    a catheter having a proximal end sized for insertion into a bladder though a urethra and a distal end opposite of the proximal end;
    a connector attached to the distal end of the catheter;
    a package sized to receive the catheter and the connector, with the package including an opening sized for removal of the catheter and the connector from the package;
    a tab placed over the opening of the package to seal the catheter and the connector inside of the package; and
    an extractor having a first portion connected to the tab and a second portion coupled to the catheter proximal of the connector; wherein the tab is removably attached over the opening of the package.

2. The catheter assembly of claim 1, wherein the tab includes an interior wall that is oriented toward the catheter when the catheter is inside the package, with the first portion of the extractor connected to an interior wall of the tab.

3. The catheter assembly of claim 1, wherein the extractor is separate from and attached to the tab.

4. The catheter assembly of claim 1, wherein the second portion of the extractor surrounds the catheter.

5. The catheter assembly of claim 1, wherein one end of the extractor is removably coupled to the package.

6. The catheter assembly of claim 1, wherein a portion of the tab includes adhesive configured for fastening the tab to a restroom surface area.

7. The catheter assembly of claim 1, wherein the tab includes a gripping portion provided with a hole sized to receive a finger of the user.

8. The catheter assembly of claim 1, wherein when the tab is removed from the opening in the package, the extractor is located between the tab and the catheter.

9. A catheter assembly comprising:
    a package defining an internal cavity, an opening communicating with the internal cavity, and a tab sealed over the opening of the package to provide a sealed internal cavity of the package;
    a catheter retained in the sealed internal cavity of the package, the catheter including a tube having a proximal end sized for insertion into a bladder though a urethra and a connector attached to a distal end of the tube; and
    an extractor having a first portion connected to the tab and a second portion coupled to the tube of the catheter proximal relative to the connector; wherein the tab is removably attached over the opening of the package.

* * * * *